United States Patent
Silver

(10) Patent No.: US 12,194,018 B2
(45) Date of Patent: *Jan. 14, 2025

(54) CANNABINOID COMPOSITIONS

(71) Applicant: SRE Wellness, Inc., New York, NY (US)

(72) Inventor: Ronald Silver, New York, NY (US)

(73) Assignee: SRE Wellness, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/375,846

(22) Filed: Oct. 2, 2023

(65) Prior Publication Data

US 2024/0285574 A1    Aug. 29, 2024

Related U.S. Application Data

(63) Continuation of application No. 16/854,800, filed on Apr. 21, 2020, now abandoned, which is a continuation-in-part of application No. 16/161,027, filed on Oct. 15, 2018, now Pat. No. 10,624,844, which is a continuation-in-part of application No. PCT/US2017/027549, filed on Apr. 14, 2017, and a continuation-in-part of application No. PCT/US2017/027550, filed on Apr. 14, 2017, and a continuation-in-part of application No. PCT/US2017/027543, filed on Apr. 14, 2017.

(60) Provisional application No. 62/328,975, filed on Apr. 28, 2016, provisional application No. 62/323,154, filed on Apr. 15, 2016.

(51) Int. Cl.
  *A61K 31/352*   (2006.01)
  *A61K 31/05*    (2006.01)
  *A61K 47/40*    (2006.01)

(52) U.S. Cl.
  CPC ............ *A61K 31/352* (2013.01); *A61K 31/05* (2013.01); *A61K 47/40* (2013.01); *A61K 2236/331* (2013.01); *A61K 2236/37* (2013.01)

(58) Field of Classification Search
  None
  See application file for complete search history.

(56) References Cited

U.S. PATENT DOCUMENTS

| | | |
|---|---|---|
| 3,140,184 A | 7/1964 | Robbins |
| 4,519,844 A | 5/1985 | Chaux et al. |
| 5,646,131 A | 7/1997 | Badwan et al. |
| 5,882,716 A | 3/1999 | Munz-Schaerer et al. |
| 6,287,603 B1 | 9/2001 | Prasad et al. |
| 6,303,662 B1 | 10/2001 | Nagahama et al. |
| 6,383,513 B1 | 5/2002 | Watts et al. |
| 7,276,516 B2 | 10/2007 | Allen et al. |
| 7,595,339 B2 | 9/2009 | Allen et al. |
| 8,906,429 B1 | 12/2014 | Kolsky |
| 8,980,941 B2 | 3/2015 | Hospodor |
| 9,259,449 B2 | 2/2016 | Raderman |
| 9,474,725 B1 | 10/2016 | Reillo et al. |
| 9,801,409 B1 | 10/2017 | Smith |
| 9,839,612 B2 | 12/2017 | Reillo et al. |
| 9,972,680 B2 | 5/2018 | Reillo et al. |
| 9,974,739 B2 | 5/2018 | Reillo et al. |
| 9,987,567 B1 | 6/2018 | Ko |
| 10,080,736 B2 | 9/2018 | Kleidon et al. |
| 10,084,044 B2 | 9/2018 | Reillo et al. |
| 10,103,225 B2 | 10/2018 | Reillo et al. |
| 10,245,525 B1 | 4/2019 | Ko |
| 10,301,242 B2 | 5/2019 | Zhang et al. |
| 10,374,036 B2 | 8/2019 | Reillo et al. |
| 10,376,551 B2 | 8/2019 | Franklin et al. |
| 10,381,440 B2 | 8/2019 | Reillo et al. |
| 10,399,005 B2 | 9/2019 | Ko |
| 10,406,453 B2 | 9/2019 | Ko et al. |
| 10,413,843 B2 | 9/2019 | Ko et al. |
| 10,617,636 B2 | 4/2020 | Silver |
| 10,624,844 B2 | 4/2020 | Silver |
| 2003/0229027 A1 | 12/2003 | Eissens et al. |
| 2003/0229029 A1 | 12/2003 | Laudadio et al. |
| 2005/0090468 A1 | 4/2005 | Jarvinen et al. |
| 2005/0153931 A1 | 7/2005 | Jarho et al. |
| 2005/0220744 A1 | 10/2005 | Kamachi et al. |
| 2007/0104741 A1 | 5/2007 | Murty et al. |
| 2009/0029020 A1 | 1/2009 | Strassburger |
| 2009/0214446 A1 | 8/2009 | Strassburger |

(Continued)

FOREIGN PATENT DOCUMENTS

| | | |
|---|---|---|
| CA | 1062949 A | 9/1979 |
| CA | 2859930 A1 | 3/2016 |

(Continued)

OTHER PUBLICATIONS

"U.S. Appl. No. 15/565,138, 312 Amendment filed Dec. 20, 2019", 3 pgs. "U.S. Appl. No. 15/565,138, Notice of Allowance mailed Nov. 27, 2019", 9 pgs.
"U.S. Appl. No. 15/565,138, Preliminary Amendment filed Jun. 12, 2019", 11 pgs.
"U.S. Appl. No. 15/565,138, Preliminary Amendment filed Oct. 6, 2017", 12 pgs.
"U.S. Appl. No. 15/565,138, PTO Response to Rule 312 Communication mailed Feb. 18, 2020", 2 pgs.
"U.S. Appl. No. 15/565,139, Preliminary Amendment filed Oct. 6, 2017", 9 pgs.
"U.S. Appl. No. 15/565,139, Restriction Requirement mailed Apr. 2, 2019", 11 pgs.
"U.S. Appl. No. 16/161,027, 312 Amendment filed Dec. 20, 2019", 3 pgs.
"U.S. Appl. No. 16/161,027, Notice of Allowance mailed Nov. 20, 2019", 10 pgs.

(Continued)

*Primary Examiner* — Michael V Meller
(74) *Attorney, Agent, or Firm* — Schwegman Lundberg & Woessner, P.A.

(57) ABSTRACT

A cannabinoid composition including a cannabinoid oil, such as THC oil or CBD oil, one or more thickeners such as gums, and a compound that forms an inclusion complex with the cannabinoid oil. The composition may include water, and in intermediate stages can include an alcohol. The composition can also include a sweetener to make it a sugar or a syrup. In some embodiments there are no other oils in the composition.

9 Claims, 7 Drawing Sheets

(56) References Cited

U.S. PATENT DOCUMENTS

| | | | |
|---|---|---|---|
| 2009/0298929 | A1 | 12/2009 | Jarho et al. |
| 2012/0114798 | A1 | 5/2012 | Zobrist |
| 2013/0029970 | A1 | 1/2013 | Sprott et al. |
| 2013/0178453 | A1 | 7/2013 | Rohde et al. |
| 2013/0196960 | A1 | 8/2013 | Rohde et al. |
| 2014/0072672 | A1 | 3/2014 | Nisbet et al. |
| 2014/0271940 | A1 | 9/2014 | Wurzer |
| 2014/0357708 | A1* | 12/2014 | Murty .............. A61K 47/10 514/454 |
| 2015/0045282 | A1 | 2/2015 | Elsohly et al. |
| 2015/0057342 | A1 | 2/2015 | Koren et al. |
| 2015/0105455 | A1 | 4/2015 | Bjorncrantz |
| 2015/0182455 | A1 | 7/2015 | Llamas |
| 2016/0000843 | A1 | 1/2016 | Lowe et al. |
| 2016/0051510 | A1 | 2/2016 | Allen et al. |
| 2016/0184258 | A1 | 6/2016 | Murty et al. |
| 2016/0324776 | A1 | 11/2016 | Glatzel |
| 2017/0232210 | A1 | 8/2017 | Boeckl et al. |
| 2018/0193392 | A1 | 7/2018 | Silver |
| 2018/0200315 | A1 | 7/2018 | Silver |
| 2018/0206518 | A1 | 7/2018 | Silver |
| 2019/0037893 | A1 | 2/2019 | Ajami et al. |
| 2019/0060227 | A1 | 2/2019 | Silver |
| 2019/0192607 | A1 | 6/2019 | Gokaraju et al. |
| 2020/0016091 | A1 | 1/2020 | Mallia et al. |
| 2020/0037638 | A1 | 2/2020 | Faraci et al. |
| 2020/0045998 | A1 | 2/2020 | Markosyan et al. |
| 2020/0197353 | A1 | 6/2020 | Artiss |
| 2020/0316014 | A1 | 10/2020 | Silver |
| 2022/0087972 | A9 | 3/2022 | Silver |

FOREIGN PATENT DOCUMENTS

| | | |
|---|---|---|
| CA | 3021093 A1 | 10/2017 |
| CN | 104544069 A | 4/2015 |
| CN | 110025595 A | 7/2019 |
| EP | 3442521 A1 | 2/2019 |
| EP | 3442522 A1 | 2/2019 |
| JP | 2019511580 A | 4/2019 |
| JP | 2019150017 A | 9/2019 |
| WO | WO-2013009928 A1 | 1/2013 |
| WO | WO-2016022936 A1 | 2/2016 |
| WO | WO-2017180948 A1 | 10/2017 |
| WO | WO-2017180953 A1 | 10/2017 |
| WO | WO-2017180954 A1 | 10/2017 |
| WO | WO-2017193110 A1 | 11/2017 |
| WO | WO-2019023803 A1 | 2/2019 |
| WO | WO-2019157592 A1 | 8/2019 |
| WO | WO-2019160945 A1 | 8/2019 |
| WO | WO-2019217800 A1 | 11/2019 |

OTHER PUBLICATIONS

"U.S. Appl. No. 16/161,027, Preliminary Amendment filed Jun. 14, 2019", 9 pgs.
"U.S. Appl. No. 16/161,027, PTO Response to Rule 312 Communication mailed Jan. 21, 2020", 2 pgs.
"U.S. Appl. No. 16/161,027, PTO Response to Rule 312 Communication mailed Mar. 23, 2020", 2 pgs.
"U.S. Appl. No. 16/161,027, Restriction Requirement mailed Nov. 15, 2019", 7 pgs.
"U.S. Appl. No. 16/854,800, Final Office Action mailed Mar. 30, 2023", 17 pgs.
"U.S. Appl. No. 16/854,800, Non Final Office Action mailed Aug. 5, 2022", 25 pgs.
"U.S. Appl. No. 16/854,800, Notice of Non-Compliant Amendment mailed May 13, 2022", 4 pgs.
"U.S. Appl. No. 16/854,800, Response filed Feb. 6, 2023 to Non Final Office Action mailed Aug. 5, 2022", 5 pgs.
"U.S. Appl. No. 16/854,800, Response filed Mar. 9, 2022 to Restriction Requirement mailed Jan. 13, 2022", 8 pgs.
"U.S. Appl. No. 16/854,800, Response filed Jul. 12, 2022 to Notice of Non-Compliant Amendment mailed May 13, 2022", 6 pgs.
"U.S. Appl. No. 16/854,800, Restriction Requirement mailed Jan. 13, 2022", 6 pgs.
"Canadian Application Serial No. 3,021,093, Office Action mailed May 25, 2023", 7 pgs.
"Cannabis XV Preparation and Stability of Tetrahydrocannabinol-8-cyclodextrin inclusion complex", Journal of Natural Products, vol. 46 No. 5, (Sep.-Oct. 1983), 633-637.
"European Application Serial No. 17783190.6, Communication Pursuant to Article 94(3) EPC mailed Jun. 21, 2023", 8 pgs.
"European Application Serial No. 17783190.6, Communication Pursuant to Article 94(3) EPC mailed Nov. 29, 2021", 8 pgs.
"European Application Serial No. 17783190.6, Extended European Search Report mailed Dec. 4, 2019", 10 pgs.
"European Application Serial No. 17783190.6, Response filed Mar. 16, 2022 to Communication Pursuant to Article 94(3) EPC mailed Nov. 29, 2021", 6 pgs.
"European Application Serial No. 17783190.6, Response filed Mar. 25, 2024 to Communication Pursuant to Article 94(3) EPC mailed Jun. 21, 2023", 10 pgs.
"European Application Serial No. 17783190.6, Response filed Jul. 6, 2020 to Extended European Search Report mailed Dec. 4, 2019", 8 pgs.
"European Application Serial No. 17783190.6, Response to Communication pursuant to Rules 161(2) and 162 EPC filed Jun. 6, 2019", 34 pgs.
"European Application Serial No. 17783191.4, Amendment filed Jun. 17, 2019", 3 pgs.
"European Application Serial No. 17783191.4, Extended European Search Report mailed Dec. 4, 2019", 10 pgs.
"European Application Serial No. 17783191.4, Noting of loss of rights pursuant to Rule 112(1) EPC mailed Aug. 7, 2020", 2 pgs.
"European Application Serial No. 17783191.4, Response to Communication pursuant to Rules 161(2) and 162 EPC filed Jun. 6, 2019", 34 pgs.
"International Application Serial No. PCT/US2017/027543, International Preliminary Report on Patentability mailed Oct. 25, 2018", 7 pgs.
"International Application Serial No. PCT/US2017/027543, International Search Report mailed Jul. 3, 2017", 2 pgs.
"International Application Serial No. PCT/US2017/027543, Written Opinion mailed Jul. 3, 2017", 5 pgs.
"International Application Serial No. PCT/US2017/027549, International Preliminary Report on Patentability mailed Oct. 25, 2018", 7 pgs.
"International Application Serial No. PCT/US2017/027549, International Search Report mailed Jul. 20, 2017", 2 pgs.
"International Application Serial No. PCT/US2017/027549, Written Opinion mailed Jul. 20, 2017", 5 pgs.
"International Application Serial No. PCT/US2017/027550, International Preliminary Report on Patentability mailed Oct. 25, 2018", 7 pgs.
"International Application Serial No. PCT/US2017/027550, International Search Report mailed Jul. 17, 2017", 2 pgs.
"International Application Serial No. PCT/US2017/027550, Written Opinion mailed Jul. 17, 2017", 5 pgs.
"Israel Application Serial No. 262350, Notification of Defects in Patent Application mailed Jul. 20, 2023", w/ English Claims, 6 pgs.
"Israel Application Serial No. 262350, Response filed May 16, 2024 to Notification of Defects in Patent Application mailed Jul. 20, 2023", W/English Claims, 11 pgs.
"Products-DeepCell Industries", [Online]. Retrieved from the Internet: <URL: https://deepcell.industries/products/>, (2016).
"Quigley's Fast-acting Cannabis Drink", downloaded Apr. 25, 2016, [Online]. Retrieved from the Internet: <URL: https://www.quigleys.com/#>, (Jan. 25, 2016).
"What is MGT Oil Really", [Online]. Retrieved from the Internet: <bulletproofexec.com>.
"Xanthan gum-Wikipedia", [Online]. Retrieved from the Internet: <URL: https://en.wikipedia.org/wiki/Xanthan_gum>, (Apr. 10, 2016).
Asprey, Dave, "What is MCT Oil Really? MCT Oil vs. Coconut Oil Explained", [Online]. Retrieved from the Internet: <URL: https://blog.bulletproof.com/what-is-mct-oil-vs-coconut-oil/>, (Sep. 8, 2015).

(56) References Cited

OTHER PUBLICATIONS

Boll, Bjorn, et al., "Comparative evaluaton of two methods for preparative fractionation of proteinaceous subvisible articles-differential centrifugation and FACS", Pharmaceutical Research, vol. 32, (2015), 3952-3964.

Bottcher, Sandra, et al., "Factors Affecting Foamed Emulsions Prepared with an Extract from Quillaja Saponaria Molina: Oil Droplet Size, Ph and Presence of Beta-Lactoglobulin", Food Biophysics (2017) 12, (Apr. 27, 2017), 250-260.

Bradford, Alina, "What is THC?", [Online]. Retrieved from the Internet: <URL: https://www.livescience.com/24553-what-is-thc.html>, (Apr. 10, 2016).

Chouhan, A.P. Singh, et al., "Modern heterogeneous catalysts for biodiesel production: A comprehensive review", Renewable and Sustainable Energy Reviews, vol. 15, Issue 9, Dec. 2011, [Online]. Retrieved from the Internet: <URL: https://www.sciencedirect.com/science/article/abs/pii/S1364032111003595>, (Sep. 22, 2011), 4378-4399.

De Sousa, Marylane, et al., "Crude Glycerol from Biodiesel Industry as Substrate for Biosurfactant Production by Bacillus subtilis ATCC 6633", Brazilian Archives of Biology and Technology, vol. 57, on.2, [Online]. Retrieved from the Internet: <URL: https://www.scielo.br/scielo.php?script=sci_arttext&pid=S1516-89132014000200019>, (Mar.-Apr. 2014).

Dorm, Drake, "Supercritical CO2 Cannabis Extraction is Safe", [Online]. Retrieved from the Internet: <URL: https://www.medicaljane.com/2014/04/11/supercritical-carbon-dioxide-co2-extraction-pure-cannabis-oil/>, (Apr. 11, 2014).

Jarho, Pekka, et al., "Hydroxypropyl-ß-cyclodextrin and its combination with hydroxypropyl-methylcellulose increases aqueous solubility of ?9-tetrahydrocannabinol", Life Sciences, vol. 63, No. 26, (Oct. 15, 1998), 381-384.

Jarzebski, Maciej, et al., "Plant Extracts Containing Saponins Affects the Stability and Biological Activity of Hempseed Oil Emulsion System", Molecules 2020, 25, 2696, (Jun. 10, 2020).

Jozwiakowski, Michael J, et al., "Aqueous solubility behavior of three cyclodextrins", Carbohydrate Research, vol. 143, (1985), 51-59.

Loftsson, Thorsteinn, "Cyclodextrins", [Online]. Retrieved from the Internet: <URL: https://notendur.hi.is/thorstlo/general.pdf>, (2004).

Macierzanka, Adam, et al., "Esterification Kinetics of Glycerol with Fatty Acids in the Presence of Zinc Carboxylates: Preparation of Modified Acylglycerol Emulsifiers", Ind. Eng. Chem. Res. 2004, 43, 24, [Online]. Retrieved from the Internet: <URL: https://pubs.acs.org/doi/abs/10.1021/ie040077m>, (Oct. 27, 2014), 7744-7753.

Magnusdottir, Audur, "Self Association and Cyclodextrin Solubilization and NSAIDs", J. Incl. Phenom. Macroc. Chem. 44,, (Oct. 1, 2002), 213-218.

Mannila, Janne, et al., "Precipitation Complexation Method Produces Cannabidiol/ß-Cyclodextrin Inclusion Complex Suitable for Sublingual Administration of Cannabidiol", Journal of Pharmaceutical Sciences, vol. 96, No. 2, (Feb. 2007).

McDonough, "Psychedelicatessen: Cannabis Cocktails", [Online]. Retrieved from the Internet: <URL: http://hightimes.com/edibles/psychedelicatessen-cannabis-cocktails/>, (May 12, 2014).

Mierjeski, Alex, "I Drank Cannabis Coffee with Seattle Baristas", [Online]. Retrieved from the Internet: <URL: https://munchies.vice.com/en_us/article/d75bk7/-cupped-cannabis-coffee-with-seattles-baristas>, (Nov. 29, 2014).

Ozturk, Bengu, et al., "Progress in Natural Emulsifiers for Utilization in Food Emulsions", Current Opinion in Food Science 2016, 7:1-6, (Aug. 4, 2015).

Panlilio, Leigh V, et al., "Combined Effects of THC and Caffeine on Working Memory in Rats", Br J Pharmacol Apr. 2012, 165 (8), (Apr. 13, 2011), 2529-2538.

Saokham, Phennapha, et al., "Solubility of cyclodextrins and drug/cyclodextrin complexes", Molecules, vol. 23, No. 1161, (2018).

Sawai, Satoru, et al., "Triterpenoid Biosynthesis and Engineering in Plants", Frontiers in Plant Science Jun. 2011 vol. 2 Article 25, [Online]. Retrieved from the Internet: <URL: https://www.frontiersin.org/articles/10.3389/fpls.2011.00025/full>, (Jun. 30, 2011), 8 pgs.

Shoyama, Y., et al., "Cannabis. XV. Preparation and Stability of ?9-Tetrahydrocannabinol-ß-Cyclodextrin Inclusion Complex", Journal of Natural Products, vol. 46 No. 5,, (Sep.-Oct. 1983), 633-637.

Specogna, Erika, et al., "Dehydration, dissolution, and melting of cyclodextrin crystals", Journal of Physical Chemistry B, vol. 119, (2015), 1433-1442.

Tobias, "Cannabis Infused Honey Tincture Video & Recipe", [Online]. Retrieved from the Internet: <URL: https://wakeandbake.co/cannabis-infused-honey-tincture-video-recipe/>, (Apr. 1, 2016).

Trotta, Francesco, et al., "Cyclodextrin-based nanosponges as drug carriers", Beilstein J. Org. Chem. 2012, 8, (Nov. 29, 2012), 2091-2099.

Upadhye, Sampada B, et al., "Preparation and Characterization of Inclusion Complexes of a Hemisuccinate Ester Prodrug of ?9-Tetrahydrocannabinol with Modified Beta-Cyclodextrins", AAPS PharmSciTech vol. 11, No. 2, (Jun. 2, 2010), 509-517.

Yang, Ying, et al., "Formation and Stability of Emulsions Using a Natural Small Molecule Surfactant: Quillaja Saponin (Q-Naturale)", Food Hydrocolloids 30, Aug. 17, 2012, (2013), 589-596.

Zhang, Ruyuan, et al., "Recent advances in polysaccharides stabilized emulsions for encapsulation and delivery of bioactive food ingredients: A review", Carbohydrate Polymers 242 (2020) 116388, (May 23, 2020).

* cited by examiner

CANNABINOID COMPOSITIONS

CROSS-REFERENCE TO RELATED APPLICATIONS

This application is a Continuation-in-Part application of U.S. patent application Ser. No. 16/161,027, filed on Oct. 15, 2018, issuing as U.S. Pat. No. 10,624,844 on Apr. 21, 2020, which application is a Continuation-in-Part application of International Application No. PCT/US2017/027550 filed Apr. 14, 2017 and from International Application No. PCT/US2017/027549 filed Apr. 14, 2017, and from International Application No. PCT/US2017/027543 filed Apr. 14, 2017 which all claim priority to and the benefit of U.S. Provisional Application No. 62/323,154 filed Apr. 15, 2016 and U.S. Provisional Application No. 62/328,975 filed Apr. 28, 2016, and the specification and claims thereof are incorporated herein by reference.

FIELD OF THE INVENTION

Embodiments of the present invention relate to a method of making *Cannabis* oil hydrophilic using emulsifiers. More particularly, embodiments of the present invention relate to a water-soluble cannabinoid composition, a cannabinoid composition with caffeine emulsifications, *Cannabis* oil infused sweeteners and elixir that may be bio-available, fast acting and highly metabolizable.

BACKGROUND OF THE INVENTION

Cannabinoids are chemical compounds found in the *Cannabis* plant that interact with receptors in the brain and body to create various effects. Herbal *Cannabis* contains over 400 compounds including over 100 cannabinoids, which are aryl-substituted meroterpenes unique to the plant genus *Cannabis*. The pharmacology of most of the cannabinoids is largely unknown but the most potent psychoactive agent, $\Delta^9$-tetrahydrocannabinol ($\Delta^9$-THC, or THC), has been isolated, synthesized and much studied due to its abundance and psychoactive attributes. Other plant cannabinoids include $\Delta^8$-THC, cannabinol and cannabidiol (CBD). These and other cannabinoids have additive, synergistic or antagonistic effects with THC and may modify its actions when herbal *Cannabis* is smoked.

The best studied cannabinoids include tetrahydrocannabinol (THC), cannabidiol (CBD) and cannabinol (CBN). These structures are shown in FIG. 1. All cannabinoids derive from cannabigerol-type compounds and differ mainly in the way this precursor is cyclized. The classical cannabinoids are derived from their respective 2-carboxylic acids (2-COOH) by decarboxylation (catalyzed by heat, light, or alkaline conditions).

The isolation of THC came from an Israeli chemist by the name of Raphael Mechoulam. In 1964, Mechoulam isolated and synthesized THC from Lebanese hashish, marking the beginning of *Cannabis* research that would lead to the discovery of many other cannabinoids, cannabinoid receptors throughout the body, and "endocannabinoids"—the THC-like compounds the human body naturally produces to maintain stability and health.

CBD and THC levels tend to vary among different plants. Marijuana grown for recreational purposes often contains more THC than CBD. However, by using selective breeding techniques, *Cannabis* breeders can create varieties with high levels of CBD and next to zero levels of THC.

Humans and many other animals have receptor systems that THC binds to, and therefore can also reap the benefits of cannabinoids for both health and enjoyment. The endocannabinoid system (or "ECS"), is a group of specialized signaling chemicals, their receptors, and the metabolic enzymes that produce and break them down. These endocannabinoid chemical signals act on some of the same brain and immune cell receptors (CB1 and CB2) that plant cannabinoids like CBD and THC act on.

THC works by binding to cannabinoid receptors concentrated in the brain and central nervous system to produce psychoactive effects. The main difference between THC and CBD, both of which are very popular cannabinoids, is in their psychoactive effects. THC elicits strong cerebral euphoria, while CBD lacks psychoactive effects altogether. This basically comes down to the fact that THC activates CB1 receptors in the human brain while CBD does not.

It is well known that cannabinoids, especially CBD and THC have many medicinal benefits. CBD's subtle effects are primarily felt in pain, inflammation, and anxiety relief, as well as other medicinal benefits. CBD also does not have any adverse side effects that may occur with consumption of THC. Unlike THC, CBD also does not cause a high. This makes CBD a significant advantage as a medicine, since health professionals prefer treatments with minimal side effects. CBD also appears to counteract the sleep-inducing effects of THC, which may explain why some strains of *Cannabis* are known to increase alertness. CBD also acts to reduce the intoxicating effects of THC, such as memory impairment and paranoia.

THC has a wide range of short-term effects which may or may not be experienced depending on the individual and their body chemistry. Some positive short-term effects of THC include: elation, relaxation, sedation, pain relief, energy, hunger, drowsiness, slowed perception of time and laughter.

There are a variety of medical conditions for which THC offers benefits. The conditions include Post Traumatic Stress Disorder, neuropathic and chronic pain, insomnia, nausea, inflammation, arthritis, migraines, Cancer, Crohn's disease, fibromyalgia, Alzheimer's disease, Multiple sclerosis, Glaucoma, Attention deficit hyperactivity disorder ("ADHD"), sleep apnea and appetite loss.

Both CBD and THC have been found to present no risk of lethal overdose. However, to reduce potential side effects, medical users are better off using *Cannabis* with higher levels of CBD.

Today the most common way to consume THC is through smoking although they can be consumed orally. However, known methods for orally administered THC have reduced bioavailability due to low absorption and high first-pass metabolism in the digestive system. Thus, there is a need for aqueous cannabinoid solutions.

Decarboxylation of the THC occurs with heating and is the key to enjoying THC, whether it is consumed by smoking or ingesting. In its raw form, *Cannabis* is non-psychoactive, with its primary cannabinoid being THCA. However, by applying heat, either when lighting it in a pipe or cooking it into oil, the THCA is converted to THC.

The invention method provides an advantageous alternative to smoking *Cannabis* by providing a water-soluble cannabinoid composition for oral ingestion that is bioavailable, highly metabolizable and fast acting.

As an aromatic terpenoid, THC has a very low solubility in water, but good solubility in most organic solvents, specifically lipids and alcohols.

The problem with edible *Cannabis* products is they take a varied amount of time to take effect due to the liver's varied ability to process the THC molecule. Depending on liver function at the time, between 2-6% of the THC is able to be metabolized. This process makes it so the THC is absorbed in the esophagus and soft tissues, making it faster acting and more highly metabolizable.

Unlike anything currently known, one or more purposes of embodiments of the present invention is to provide a water-soluble cannabinoid composition, and/or a cannabinoid emulsification (with or without caffeine), and/or *Cannabis* infused sweeteners and *Cannabis* infused elixirs to create *Cannabis* oil infused products for medical and recreational use that are bioavailable, fast acting and highly metabolized, with consistent results that take place in a consistent amount of time. In general, elixirs are healing botanicals known to address specific imbalances yet, they are not necessarily teaching the body to mimic the healing chemistry in order for the body to continue healing. Also, elixirs are made with delicious flavoring agents, flowers and healthy sweeteners, as well as use a different ratio of medicinal potency. Elixirs are usually a 1:3 or 1:4 in liquid to herb extraction.

In making the sweeteners and elixirs according a method of the present invention, a method to make *Cannabis* oil water-soluble is used which uses a combination of emulsifiers and variations in time and temperature of the reaction steps. The process results in a *Cannabis* infused sweeteners and elixirs which provide fast acting, bioavailability and highly metabolizable delivery of the *Cannabis* oil, either alone or in combination with other edible products.

Another purpose of the invention is to provide a line of *Cannabis* oil infused sugars and elixirs that share a base of coconut water infused with coconut fat and to sell the products to wholesale distributors for retail sale in legal dispensaries.

A purpose of an embodiment of the invention is to provide a method to make *Cannabis* oil water-soluble using a combination of emulsifiers and variations in time and temperature of the reaction steps. One result of the process is a water-soluble, hydrophilic cannabinoid composition, and/or a cannabinoid emulsification and/or *Cannabis* infused sweeteners and *Cannabis* infused elixirs which can be used in a variety of edible products providing fast acting, bioavailability and highly metabolizable delivery of the *Cannabis* oil.

Another purpose of the invention is to provide a line of *Cannabis* oil and caffeine edible products that share a base of coconut water infused with coconut fat and to sell the products to wholesale distributors for retail sale in legal dispensaries.

Another purpose of the invention is to provide a line of *Cannabis* oil and caffeine infused sugars and elixirs that share a base of coconut water infused with coconut fat and to sell the products to wholesale distributors for retail sale in legal dispensaries.

More specifically a purpose of the invention is to use the water-soluble cannabinoid composition, and/or a cannabinoid emulsification and/or a *Cannabis* infused sweeteners and elixirs to treat Post Traumatic Stress Disorder, neuropathic and chronic pain, insomnia, nausea, inflammation, arthritis, migraines, Cancer, Crohn's disease, fibromyalgia, Alzheimer's disease, Multiple sclerosis, Glaucoma, Attention deficit hyperactivity disorder ("ADHD"), sleep apnea and appetite loss.

Yet another purpose of an embodiment of the water-soluble *Cannabis* oil composition, and/or emulsification, and/or sugars and elixirs is to treat pain, inflammation, and anxiety relief.

More specifically, the water-soluble *Cannabis* oil composition, and/or the emulsification, and/or the sugars and elixirs can be combined with chocolate and/or liquor to create edible products.

Yet another purpose of embodiments of the present invention provides that the composition, emulsification, and/or sugars and elixirs can be used to produce other edible products at home or professionally with predictable results, including being fast-acting, and highly metabolizable, which are referred to herein as super-charged. This lets consumers know that the invention products have markedly different results than other products. These compositions can be marketed in many forms, both in retail and wholesale manufacturing, as well as aiding companies with quality products to use for research and development.

SUMMARY OF THE INVENTION

In one or more embodiments of the present invention, the above purposes, as well as others which will be apparent, are achieved generally by a method of making *Cannabis* oil hydrophilic by using a combination of emulsifiers and variations in time and temperature of the reaction steps, and/or cannabinoid emulsification made of at least one emulsifying agent; an aqueous vehicle; a base oil; *Cannabis* oil; and caffeine, and/or *Cannabis* infused sweetener comprising *Cannabis* oil; at least one emulsifying agent selected from the group consisting of xanthan gum, guar gum, lecithin, carrageen, monoglycerides, natural emulsifiers and organic emulsifiers that are safe for ingestion by humans and a sweetener. The resulting cannabinoid emulsification is bio-available, highly metabolizable and fast acting when ingested by the user.

In one embodiment, the specific steps in making the *Cannabis* oil hydrophilic include first heating a base oil in the range of about 120 to 220° F. The *Cannabis* oil is added to this heated oil (pre heating or post heating) to create a mixture which is then blended at a high speed. At least one emulsifying agent is added to the hot mixture while blending is continued. Water is then added to form the composition wherein the *Cannabis* oil is hydrophilic and is soluble in water.

This method modifies normally hydrophobic, or "water-repelling", *Cannabis* oil into a hydrophilic *Cannabis* oil alone or when combined with one or more of the following: an emulsification, sweetener/sugar and/or elixir that is bio-available, highly metabolizable and fast acting when ingested by the user. The *Cannabis* oil produced by this method is suitable for use in emulsifications and a component of sugars and elixirs.

It is a preferred process parameter that while blending the mixture it is maintained at a temperature in the range of about 120 to 220° F.

In one embodiment, a sweetener used is selected from the group consisting of white sugar, cane sugar, raw sugar, fructose, turbinado sugar, coconut sugar, date sugar, liquid stevia, liquid sugar, powdered sugar, brown sugar, muscovado sugar, honey, agave and other like sweeteners. The sweetener component is present in the range of about 98% to about 99.88% of the *Cannabis* infused sweetener. Alternatively, the sweetener is present in the range of about 50%-60%, 60-70%, 70-80%, 80-90% or 90-99.9% for example.

At least one emulsifying agent is used in the invention process which is selected from the group consisting of xanthan gum, guar gum, cyclodextrin, lecithin, carrageen, monoglycerides, natural emulsifiers and organic emulsifiers that are safe for ingestion by humans.

A *Cannabis* oil is selected from the group consisting of tetrahydrocannabinol (THC), cannabidiol (CBD) and other cannabinoid oils isolated from the marijuana plant. The *Cannabis* oil is present in the range of about 1.5 mg to 20 mg per gram of sweetener.

The emulsifying agent is present in the range of about 0.12% to 2% of the total sweetener. In preferred embodiments, the emulsifying agent is a combination of at least two emulsifying agents which can be the same or different. In a preferred embodiment, the emulsifying agents include cyclodextrin in combination with at least one selected from the group consisting of xanthan gum, guar gum, lecithin, carrageen, monoglycerides, natural emulsifiers and organic emulsifiers that are safe for ingestion by humans.

The aqueous vehicle is selected from the group consisting of coconut water, fruit juice, milk and water. The aqueous vehicle is in the range of about 60% to 99.9% of the emulsification. The preferred vehicle is coconut water. Alternatively, the aqueous vehicle is present in the range of about 50%-60%, 60-70%, 70-80%, 80-90% or 90-99.9% for example.

The base oil is selected from the group consisting of vegetable glycerine, almond oil, avocado oil, canola oil, coconut oil, corn oil, cottonseed oil, grapeseed oil, hazelnut oil, olive oil, extra virgin olive oil, palm oil, peanut oil, palm seed oil, pumpkin seed oil, safflower oil, sesame oil, soy oil, sunflower oil, vegetable oil and walnut oil and any oil high in saturated fats. The base oil is preferably in the range of about 0.1% to 40% of the emulsification. Alternatively, the base oil is present in the range of about 0.1%-5%, 5-10%, 10-20%, 20-30% or 30-40% for example.

The *Cannabis* oil used in the invention is in a pure state. The *Cannabis* oil used can be extracted from the marijuana plant by CO2 extraction, water extraction, butane extraction and extraction methods that leave a zero testing for residuals.

The *Cannabis* oil used in the invention is selected from the group consisting of tetrahydrocannabinol (THC), cannabidiol (CBD) and other cannabinoid oils isolated from the marijuana plant.

In a preferred embodiment, a *Cannabis* infused elixir is provided comprising *Cannabis* oil; at least one emulsifying agent; a sweetener selected from the group consisting of white sugar, cane sugar, raw sugar, fructose, turbinado sugar, coconut sugar, date sugar, liquid stevia, liquid sugar, powdered sugar, brown sugar, muscovado sugar, honey, agave and other like sweeteners and flavoring extracts or fruit syrups.

The sweetener is present in the range of about 98% to 99.8% of the elixir.

The *Cannabis* infused elixir includes *Cannabis* oil is bio-available, highly metabolizable and fast acting when ingested by the user.

As in the sweetener embodiment, the *Cannabis* oil used in the elixir is selected from the group consisting of tetrahydrocannabinol (THC), cannabidiol (CBD) and other cannabinoid oils isolated from the marijuana plant. The *Cannabis* oil is present in the range of about 3 mg to 50 mg per ounce of elixir.

The *Cannabis* oil and/or elixir is added to the mixture or a drink solution, such as a carbonated or flat water solution, in the range of about 5 mg to 20 mg per 2 ounces of the composition or a ratio between about 1:3 to 1:4 to create a liquid beverage. The base oil is present in the range of about 0.5 grams to 5 grams of base oil per about 1 ounce of the composition.

The emulsifying agent is in the range of about 0.15% and about 2% of the total volume of the emulsification and/or the emulsifying agent is present in the range of about 0.15% to about 2% of the elixir.

The invention also provides a water-soluble cannabinoid composition that is bioavailable, fast acting and highly metabolizable.

The emulsifying agent is selected from the group consisting of xanthan gum, guar gum, cyclodextrin, lecithin, carrageen, monoglycerides, natural emulsifiers and organic emulsifiers that are safe for ingestion by humans.

The base oil in the cannabinoid composition is preferably selected from the group consisting of vegetable glycerine, coconut oil and any oil high in saturated fats. However, other nut oils such as almond oil, avocado oil, canola oil, coconut oil, corn oil, cottonseed oil, grapeseed oil, hazelnut oil, olive oil, extra virgin olive oil, palm oil, peanut oil, palm seed oil, pumpkin seed oil, safflower oil, sesame oil, soy oil, sunflower oil, vegetable oil and walnut oil can be used as the base oil.

The *Cannabis* oil in the composition is in a pure state that has been extracted from the marijuana plant by CO2 extraction, water extraction, butane extraction and extraction methods that leave a zero testing for residuals.

The *Cannabis* oil in the composition is selected from the group consisting of tetrahydrocannabinol (THC), cannabidiol (CBD) and other cannabinoid oils isolated from the marijuana plant.

Other ingredients such as chocolate and liquor can be added to the composition to provide different flavor profiles.

In a preferred embodiment the emulsifying agent is a combination of at least two emulsifying agents. In a most preferred embodiment cyclodextrin is used in combination with at least one other emulsifying agent selected from the group consisting of xanthan gum, guar gum, lecithin, carrageen, monoglycerides, natural emulsifiers and organic emulsifiers that are safe for ingestion by humans.

The *Cannabis* oil in the emulsification is in the range of about 5 mg to 30 mg per 2 ounces of the emulsification.

Caffeine is present in one embodiment of the emulsification in the range of about 10 to 300 mg per 2 ounces of the emulsification. The caffeine can be in anhydrous form.

In the emulsification the base oil to aqueous vehicle ratio is between about 1 to 10 grams of base oil per about 2 ounces of the emulsification.

The invention also provides a method for making cannabinoid emulsifications comprising the steps of heating a base oil, preferably coconut oil, to between about 120 to 220 degrees F. Adding at least one emulsifying agent, caffeine and *Cannabis* oil to an aqueous vehicle and adding to the heated coconut oil to create a mixture. Blending the mixture in a high speed machine, while holding the temperature between about 120 to 220 degrees F. to emulsify the mixture and then adding caffeine to the mixture.

The emulsifying agents are added in an amount between 0.15% and 2% of the total volume of the mixture and are selected from the group consisting of xanthan gum, guar gum, cyclodextrin, lecithin, carrageen, monoglycerides, natural emulsifiers and organic emulsifiers that are safe for ingestion by humans.

The hot mixture is blended at high speed for between 30 seconds and 2 minutes. The resulting cannabinoid emulsification is bio-available, highly metabolizable and fast acting when ingested by the user.

In preferred embodiments the emulsifying agent is a combination of at least two emulsifying agents. In a most preferred embodiment the emulsifying agent is a combination of xanthan gum and cyclodextrin, where the cyclodextrin and xanthan gum are each present in the amount of 0.12 to 2%.

An embodiment of the present invention is a cannabinoid infused ingestible composition comprising a cannabinoid oil; a compound that forms an inclusion complex with the cannabinoid oil; and a thickener; wherein the cannabinoid oil is the only oil in the composition. The composition preferably further comprises a sweetener. The sweetener is preferably selected from the group consisting of white sugar, cane sugar, raw sugar, fructose, turbinado sugar, coconut sugar, date sugar, stevia, liquid stevia, liquid sugar, powdered sugar, brown sugar, muscovado sugar, maple sugar, honey, and agave. The compound preferably comprises cyclodextrin. The thickener preferably comprises a gum. The gum preferably comprises xanthan gum. The cannabinoid preferably comprises tetrahydrocannabinol (THC) and/or cannabidiol (CBD). The cannabinoid is preferably bio-available, highly metabolizable and fast acting when ingested. The compound and the thickener each preferably comprise about 0.12% to 2% of the composition. The composition preferably comprises from about 0.01% to 4% of both the compound and the thickener, more preferably from about 0.15% to 3% of both the compound and the thickener. The composition preferably comprises equal percentages of the compound and the thickener.

Another embodiment of the present invention is a cannabinoid infused composition consisting essentially of a cannabinoid oil; an alcohol; water; a compound that forms an inclusion complex with the cannabinoid oil; and a thickener. The compound preferably comprises cyclodextrin. The thickener preferably comprises a gum. The gum preferably comprises xanthan gum. The cannabinoid preferably comprises tetrahydrocannabinol (THC) and/or cannabidiol (CBD). The cannabinoid is preferably bio-available, highly metabolizable and fast acting when ingested. The compound and the thickener each comprise 0.12% to 2% of the composition. The composition preferably comprises about 0.01% to 4% of both the compound and the thickener, and more preferably about 0.15% to 3% of both the compound and the thickener. The composition preferably comprises equal percentages of the compound and the thickener.

Another embodiment of the present invention is a cannabinoid infused composition consisting essentially of a cannabinoid oil; water; a compound that forms an inclusion complex with the cannabinoid oil; a thickener; and a sweetener. The sweetener is preferably selected from the group consisting of white sugar, cane sugar, raw sugar, fructose, turbinado sugar, coconut sugar, date sugar, stevia, liquid stevia, liquid sugar, powdered sugar, brown sugar, muscovado sugar, maple sugar, honey, and agave. The compound preferably comprises cyclodextrin. The thickener preferably comprises a gum. The gum preferably comprises xanthan gum. The cannabinoid preferably comprises tetrahydrocannabinol (THC) and/or cannabidiol (CBD). The compound and the thickener each preferably comprise about 0.12% to 2% of the composition. The composition preferably comprises about 0.01% to 4% of both the compound and the thickener, and more preferably about 0.15% to 3% of both the compound and the thickener. The composition preferably comprises equal percentages of the compound and the thickener.

Another embodiment of the present invention is a cannabinoid infused composition consisting essentially of a cannabinoid oil; a compound that forms an inclusion complex with the cannabinoid oil; a thickener; and a sweetener. The sweetener is preferably selected from the group consisting of white sugar, cane sugar, raw sugar, fructose, turbinado sugar, coconut sugar, date sugar, stevia, liquid stevia, liquid sugar, powdered sugar, brown sugar, muscovado sugar, maple sugar, honey, and agave. The compound preferably comprises cyclodextrin. The thickener preferably comprises a gum. The gum preferably comprises xanthan gum. The cannabinoid preferably comprises tetrahydrocannabinol (THC) and/or cannabidiol (CBD). The compound and the thickener each preferably comprise about 0.12% to 2% of the composition. The composition preferably comprises about 0.01% to 4% of both the compound and the thickener, and more preferably about 0.15% to 3% of both the compound and the thickener. The composition preferably comprises equal percentages of the compound and the thickener.

Other objects, features and advantages of the present invention will be apparent when the detailed description of the preferred embodiments of the invention is considered which should be construed in an illustrative and not limiting sense.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings.

DETAILED DESCRIPTION OF THE INVENTION

Figure 1:
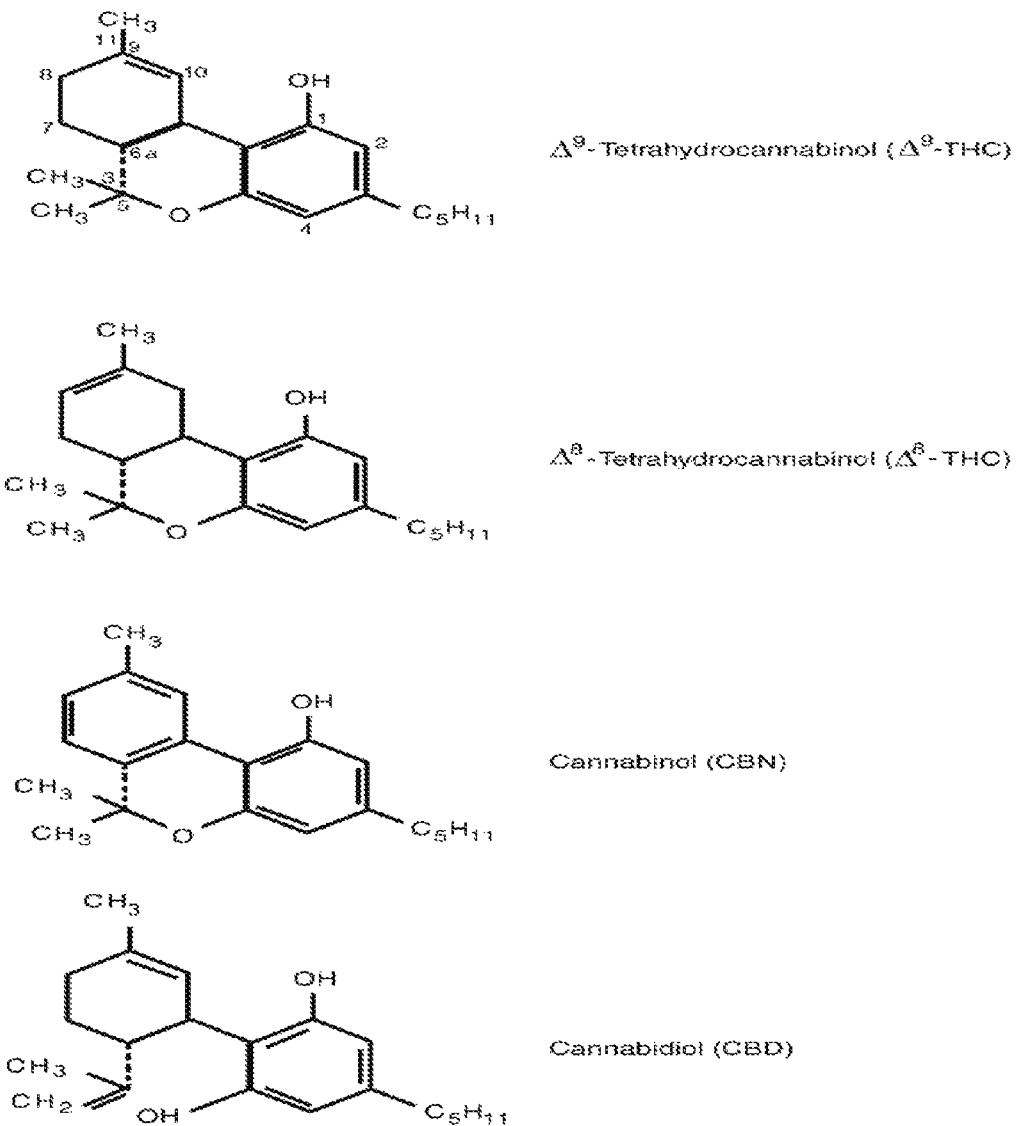
FIG. 1 is the formula for THC, cannabinol and cannabidiol and structure.

One embodiment of the present invention provides a method of making *Cannabis* oil hydrophilic. The process of the invention modifies normally hydrophobic, or "water-repelling", *Cannabis* oil into hydrophilic *Cannabis* oil that is bio-available, highly metabolizable and fast acting when ingested by the user.

Another embodiment provides a unique emulsified combination of *Cannabis* oil, caffeine, and a base oil and aqueous vehicle, which are respectively, preferably coconut oil, and coconut water. Coconut oil is one of the best sources of excellent fatty acids. Emulsified with coconut water, *Cannabis* oil and caffeine provide a beneficial experience for people experiencing a variety of ailments: insomnia, muscle aches, anxiety, etc., or are in recovery from surgery, or in chemotherapy. The emulsification makes the *Cannabis* oil molecules water-soluble, by modification from its normal hydrophobic state into a hydrophilic ("water-loving"), which makes the *Cannabis* oil bioavailable, faster acting, and more highly metabolizable.

Yet another embodiment provides a *Cannabis* infused sweetener comprising *Cannabis* oil; at least one emulsifying agent selected from the group consisting of xanthan gum, guar gum, lecithin, carrageen, monoglycerides, natural emulsifiers and organic emulsifiers that are safe for ingestion by humans and a sweetener; and *Cannabis* infused elixir comprising *Cannabis* oil; at least one emulsifying agent; a sweetener selected from the group consisting of white sugar, cane sugar, raw sugar, fructose, turbinado sugar, coconut sugar, date sugar, liquid stevia, liquid sugar, powdered sugar, brown sugar, muscovado sugar, honey, agave and other like sweeteners and flavoring extracts or fruit syrups.

In one instance, both sweetener and elixir embodiments the *Cannabis* oil therein has been modified from its normal hydrophobic state into a hydrophilic ("water-loving") state that is bio-available, highly metabolizable and fast acting when ingested by the user.

Bioavailability refers to the degree to which food nutrients, in this invention, *Cannabis* oil, are available for absorption and utilization in the body. Bioavailability typically applies to nutrients and drugs which pass through first-pass metabolism, i.e. orally consumed substances. Anything absorbed in the gut first passes through the liver before reaching the rest of the circulation, and both the gut and liver may metabolize it to some extent.

Metabolizable refers to the process of changing food/substances into a form that can be used by your body.

The process steps of an embodiment of the invention include first heating a base oil in the range of about 120 to 220° F. The *Cannabis* oil is added to this heated oil to create a mixture which is then blended at a high speed. At least one emulsifying agent is added to the hot mixture while blending is continued. Water is then added to form the composition wherein the *Cannabis* oil is hydrophilic and is soluble in water.

It is a preferred process parameter that while blending the mixture it is maintained at a temperature in the range of about 120 to 220° F.

The cannabinoid emulsification embodiment of the invention is made of at least one emulsifying agent; an aqueous vehicle; a base oil; *Cannabis* oil; and caffeine.

Emulsifiers

Emulsions are produced by dispersing normally unmixable material into another by mixing, colloidal milling or homogenization. The surface-active qualities of emulsifiers of the invention make them effective emulsifying agents that reduce mixing time and maintain the stability of the dispersion.

The emulsifying agent in the invention is present in the range of about 0.15% to 2% of the composition. At least one emulsifying agent is used in the invention process which is selected from the group consisting of xanthan gum, guar gum, cyclodextrin, lecithin, carrageen, monoglycerides, natural emulsifiers and organic emulsifiers that are safe for ingestion by humans. In preferred embodiments, the emulsifying agent is a combination of at least two different emulsifying agents.

*Cannabis* oil, including THC and CBD, are not water-soluble, so it needs to be "trapped" in something with dual polarity—that is, a compound that reconciles the fact that water is polar and the cannabinoid is not. The emulsifiers provide this. Once trapped in the compound, the THC has new de facto properties, like the ability to dissolve in water, distribute itself evenly, and stay suspended in the solution. It also displays increased bioavailability: while the same amount of *Cannabis* oil in an edible can take up to two hours to reach the bloodstream, the effects of water-soluble *Cannabis* oil dissolved in water can be felt more acutely, in as little as 10 minutes.

It is known that cannabinoids are soluble in fat. It is also known that only water-soluble substances can pass the intestine membrane. Fat is itself not water-soluble because it is like cannabinoids, uncharged. Fat absorption into the membrane requires substances with a dipole character to build up vehicles which can connect at the outer surface with water (charged side) and at the inner surface with the fat and the THC (uncharged side).

The specific emulsifiers used in the invention are detailed below.

Xanthan Gum

Figure 2:
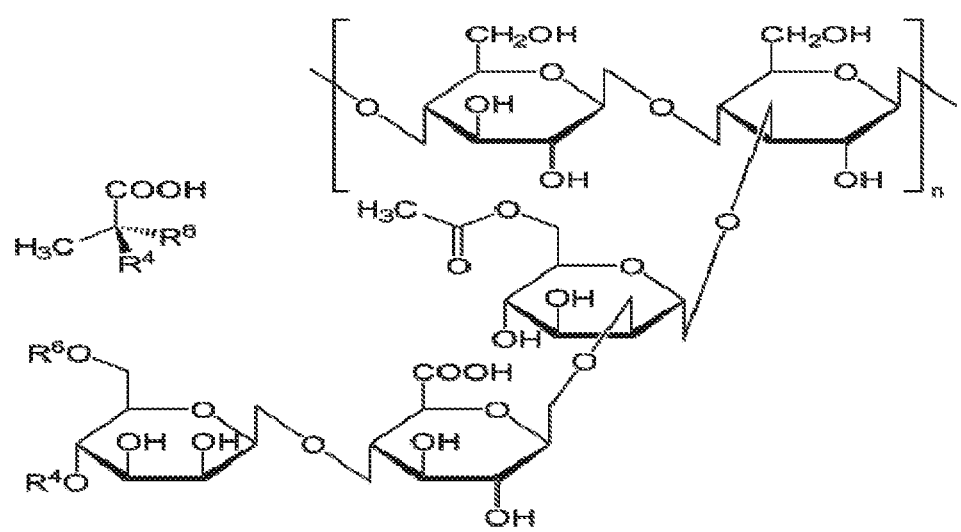
FIG. 2 is the structure for Xanthan Gum.

Xanthan gum, which is also called xanthene, has the chemical formula $C_{13}H_{10}O$. Its molecular weight is 182.22 grams/mol. FIG. 2 shows the chemical structure of xanthan gum.

In general, xanthan gum is a substance made by fermenting bacteria with sugars. It is an additive found in both foods and medicines. As a food additive, this substance is utilized either as a thickener or stabilizer. This compound has a variety of uses in medicine, such as in the treatment of diabetes, cholesterol and dry mouth.

Specifically, xanthan gum is a polysaccharide secreted by the bacterium *Xanthomonas campestris*. Its known uses, prior to the invention, is as a food additive and rheology modifier, commonly used as a food thickening agent (in salad dressings, for example) and a stabilizer (in cosmetic products, for example, to prevent ingredients from separating). As seen in FIG. 1, it is composed of pentasaccharide repeat units, comprising glucose, mannose, and glucuronic acid in the molar ratio 2:2:1. It is produced by the fermentation of glucose, sucrose, or lactose. After a fermentation period, the polysaccharide is precipitated from a growth medium with isopropyl alcohol, dried, and ground into a fine powder. Later, it is added to a liquid medium to form the gum.

Guar Gum

Figure 3:
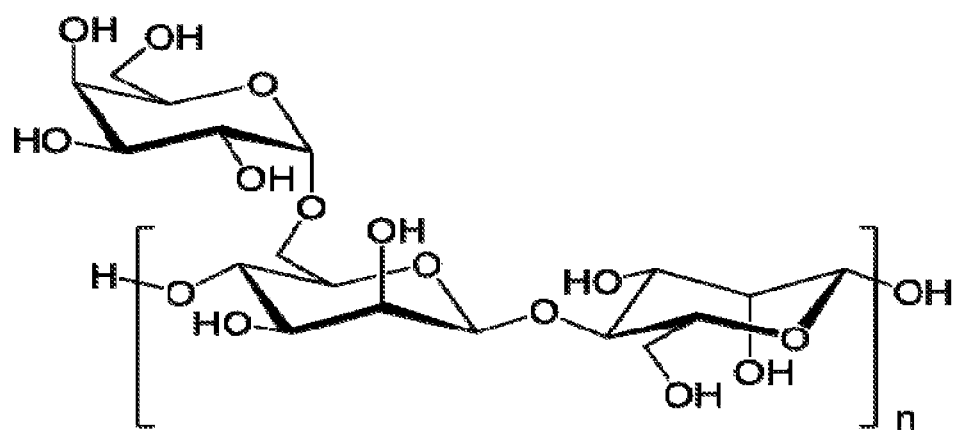
FIG. 3 is the structure of Guar Gum.

Chemically, guar gum is a polysaccharide composed of the sugars galactose and mannose. FIG. 3 shows that the backbone is a linear chain of β1,4-linked mannose residues to which galactose residues are 1,6-linked at every second mannose, forming short side-branches.

In water, guar gum is nonionic and hydrocolloidal. It is not affected by ionic strength or pH, but will degrade at extreme pH and temperature (e.g. pH 3 at 50° C.). It remains stable in solution over pH range of about 5-7. Strong acids cause hydrolysis and loss of viscosity, and alkalis in strong concentration also tend to reduce viscosity. It is insoluble in most hydrocarbon solvents. The viscosity attained is dependent on time, temperature, concentration, pH, rate of agitation and practical size of the powdered gum used. The lower the temperature, the lower the rate at which viscosity increases and the lower the final viscosity. Above 80°, the final viscosity is slightly reduced. The finer guar powders swell more rapidly than coarse powdered gum. Guar gum has almost eight times the water-thickening potency of cornstarch-only a very small quantity is needed for producing sufficient viscosity. Thus, it can be used in various multiphase formulations: as an emulsifier because it helps to prevent oil droplets from coalescing, and/or as a stabilizer because it helps to prevent solid particles from settling.

Cyclodextrin

Cyclodextrins are a group of structurally related natural products formed during bacterial digestion of cellulose.

These cyclic oligosaccharides consist of (α-1,4)-linked α-D-glucopyranose units and contain a somewhat lipophilic central cavity and a hydrophilic outer surface. Due to the chair conformation of the glucopyranose units, the cyclodextrins are shaped like a truncated cone rather than perfect cylinders. The hydroxyl functions are oriented to the cone exterior with the primary hydroxyl groups of the sugar residues at the narrow edge of the cone and the secondary hydroxyl groups at the wider edge. The central cavity is lined by the skeletal carbons and ethereal oxygens of the glucose residues, which gives it a lipophilic character. The polarity of the cavity has been estimated to be similar to that of an aqueous ethanolic solution.

The natural α-, β- and γ-cyclodextrin (αCD, βCD and γCD) consist of six, seven, and eight glucopyranose units, respectively. The natural cyclodextrins, in particular βCD, are of limited aqueous solubility meaning that complexes resulting from interaction of lipophiles with these cyclodextrin can be of limited solubility resulting in precipitation of solid cyclodextrin complexes from water and other aqueous systems. In fact, the aqueous solubility of the natural cyclodextrins is much lower than that of comparable acyclic saccharides. This is thought to be due to relatively strong intermolecular hydrogen bonding in the crystal state. Substitution of any of the hydrogen bond forming hydroxyl groups, even by lipophilic methoxy functions, results in dramatic improvement in their aqueous solubility. Water-soluble cyclodextrin derivatives of commercial interest include the hydroxypropyl derivatives of βCD and γCD, the randomly methylated β-cyclodextrin (RMβCD), and sulfobutylether β-cyclodextrin sodium salt (SBEβCD).

Figure 4:
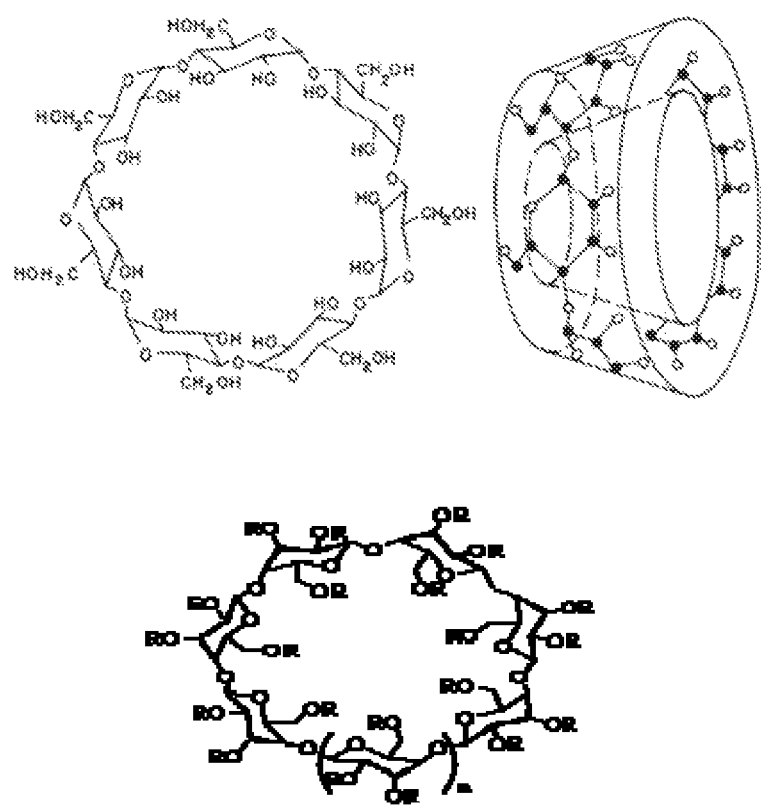
FIG. 4 is a chemical structure and the molecular shape of B-cyclodextrin (BCD)
Figure 5:
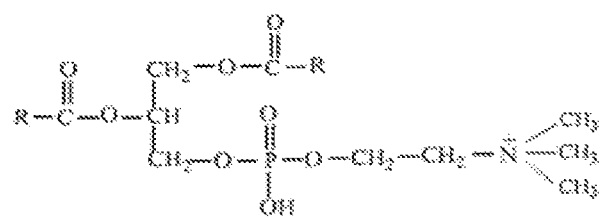
FIG. 5 is a chemical structure of Lecithin.
Figure 6:
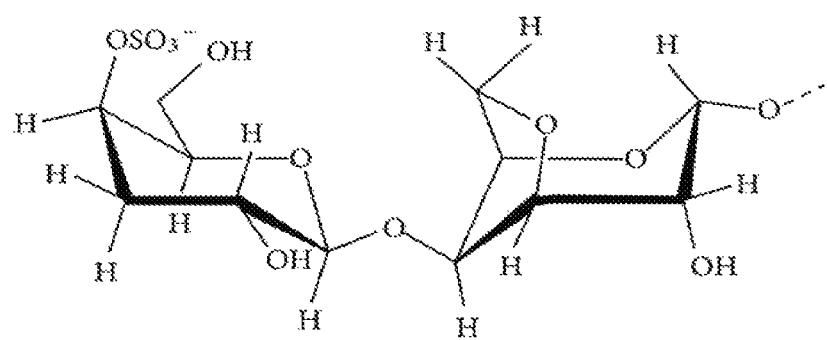
FIG. 6 is a chemical structure of Carrageen (kappa)
Figure 7:
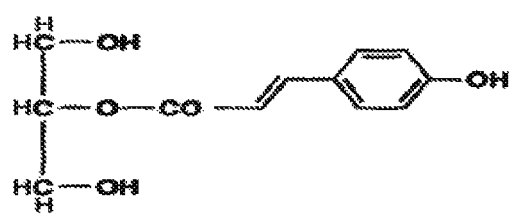
FIG. 7 is a chemical structure of a monoglyceride.

FIG. 4 and Table 1 were taken from an article entitled "Cyclodextrins" (A. Magnúsdóttir, M. Másson and T. Loftsson, J. Incl. Phenom. Macroc. Chem. 44, 213-218, 2002).

TABLE 1

| Water solubility of cyclodextrins. | | | | | |
|---|---|---|---|---|---|
| Cyclodextrin | n | R=H or | Subst.[a] | MW[b] (Da) | Solubility in water[c] (mg/L) |
| α-Cyclodextrin (αCD) | 0 | —H | 0 | 972 | 145 |
| β-Cyclodextrin (βCD) | 1 | —H | 0 | 1135 | 18.5 |
| 2-Hydroxypropyl-β-cyclodextrin (HPβCD; Kleptose ® HPB) | 1 | —CH$_2$CHOHCH$_3$ | 0.65 | 1400 | >600 |
| Sulfobutylether β-cyclodextrin sodium salt (SBEβCD; Captisol ®) | 1 | —(CH$_2$)$_4$SO$_3^-$Na$^+$ | 0.9 | 2163 | >500 |
| Randomly methylated β-cyclodextrin (RMβCD) | 1 | —CH$_3$ | 1.8 | 1312 | >500 |
| γ-Cyclodextrin (γCD) | 2 | —H | 0 | 1297 | 232 |
| 2-Hydroxypropyl-γ-cyclodextrin (HPγCD) | 2 | —CH$_2$CHOHCH$_3$ | 0.6 | 1576 | >500 |

[a]Average number of substituents per glucose repeat unit;.
[b]MW: Molecular weight;
[c]Solubility in pure water at approx. 25° C.

Cyclodextrins create highly concentrated and water-soluble granules. Cyclodextrins are circular structures of sugar molecules that are known to absorb other compounds into their center. They form inclusion complexes with poorly water-soluble compounds. Acting like a molecule magnet, cyclodextrins absorb other molecules and assume their properties. These molecules can absorb up to 60% of their weight in alcohol while remaining in powdered form. It isn't until you mix them with water that they dissolve.

Experiments with THC-cyclodextrin compounds increase THC water solubility by nearly 1000 times. For this reason, in preferred embodiments, the emulsifying agent is a combination of at least two different emulsifying agents with at least one being cyclodextrin and the other emulsifying agent selected from the group consisting of xanthan gum, guar gum, lecithin, carrageen, monoglycerides, natural emulsifiers and organic emulsifiers that are safe for ingestion by humans.

It is noted that cyclodextrin is very expensive and some versions even cause unwanted side effects when ingested. In the invention a lesser amount of cyclodextrin is used in combination with other emulsifiers that are less costly to provide the same or better solubility results. This provides an economic solution to using a lesser amount of cyclodextrin with the benefits at lower cost.

Lecithin

Lecithins are used in the invention as emulsifiers. They are surface-active; simultaneous hydrophilic (water-loving) and hydrophobic (water-repelling) properties enable lecithins to make stable blends of materials that otherwise do not mix easily and tend to separate.

Lecithin is a generic term to designate any group of yellow-brownish fatty substances occurring in animal and plant tissues, which are amphiphilic-they attract both water and fatty substances (and so are both hydrophilic and lipophilic). Lecithins are generally used for smoothing food textures, dissolving powders (emulsifying), homogenizing liquid mixtures, and repelling sticking materials. Lecithins are composed of phosphoric acid with choline, glycerol or other fatty acids usually glycolipids or triglyceride. Glycerophospholipids in lecithin include phosphatidylcholine, phosphatidylethanolamine, phosphatidylinositol, phosphatidylserine, and phosphatidic acid.

When added to *Cannabis* coconut oil lecithin increases absorption of THC and other cannabinoids into the cell membranes and speeds up the process.

Carrageen

Carrageens are a family of linear sulphated polysaccharides that are extracted from red edible seaweeds. They are widely used in the food industry, for their gelling, thickening, and stabilizing properties. Their main application is in dairy and meat products, due to their strong binding to food proteins. There are three main varieties of carrageenan, which differ in their degree of sulphation. Kappa-carrageenan has one sulphate group per disaccharide, Iota-carrageenan has two, and Lambda-carrageenan has three.

Monoglycerides

Monoglycerides are a class of glycerides which are composed of a molecule of glycerol linked to a fatty acid via an ester bond. As glycerol contains both primary and secondary alcohol groups two different types of monoglycerides may be formed; 1-monoacylglycerols where the fatty acid is attached to a primary alcohol, or a 2-monoacylglycerols where the fatty acid is attached to the secondary alcohol.

Monoglycerides are primarily used as surfactants, usually in the form of emulsifiers. Together with diglycerides, monoglycerides are commonly added to commercial food products in small quantities which helps to prevent mixtures of oils and water from separating.

Base Oil

The base oil is present in the range of about 0.5 grams to 5 grams of base oil per 1 ounce of the composition.

The base oil is preferably in the range of about 0.1% to 40% of the emulsification.

The base oil is preferably selected from the group consisting of vegetable glycerine, coconut oil and any oil high in saturated fats. Nut oils are also used in the invention process. The nut oils are selected from the group consisting of almond oil, avocado oil, canola oil, coconut oil, corn oil, cottonseed oil, grapeseed oil, hazelnut oil, olive oil, extra virgin olive oil, palm oil, peanut oil, palm seed oil, pumpkin seed oil, safflower oil, sesame oil, soy oil, sunflower oil, vegetable oil and walnut oil.

Aqueous Vehicle

An aqueous vehicle is selected from the group consisting of coconut water, fruit juice, milk and water. The aqueous vehicle is in the range of about 60% to 99.9% of the emulsification. The preferred vehicle is coconut water.

In the emulsification the base oil to aqueous vehicle ratio is between about 1 to 10 grams of base oil per 2 ounces of the emulsification.

Cannabis Oil

The Cannabis oil used in embodiments of the invention is in a pure state. This is important since the intended end use of the products of the invention are to be ingested by humans for medical or recreational use, where permitted.

The Cannabis oil used can be extracted from the marijuana plant by CO2 extraction, water extraction, butane extraction and extraction methods that leave a zero testing for residuals. Representative structures of the Cannabis oil are illustrated in FIG. 1.

The Cannabis oil used in an embodiment of the invention is selected from the group consisting of tetrahydrocannabinol (THC), cannabidiol (CBD) and other cannabinoid oils isolated from the marijuana plant.

For example, the Cannabis oil in the emulsification is in the range of about 5 mg to about 30 mg per about 2 ounces of the emulsification. The Cannabis oil in the sweetener is present in the range of about 1.5 mg to about 20 mg per gram of sweetener. The Cannabis oil present in the elixir is in the range of about 3 mg to about 50 mg per ounce of elixir. In one embodiment, the Cannabis oil is not completely emulsified. The Cannabis oil remaining un-emulsified is absorbed by the body at a different/longer rate than the emulsified Cannabis oil.

Caffeine may be present/added in an embodiment of an emulsification in the range of about 10 to about 300 mg per about 2 ounces of the emulsification. The caffeine can be in anhydrous form.

Sweetener

The Cannabis oil is added to the mixture and is present in the range of about 5 mg to 20 mg per about 2 ounces of the composition.

The sweetener is used in both the infused sweetener and white sugar, cane sugar, raw sugar, fructose, turbinado sugar, coconut sugar, date sugar, liquid stevia, liquid sugar, powdered sugar, brown sugar, muscovado sugar, honey, agave and other like sweeteners. The sweetener component is present in the range of about 98% to about 99.88% of the Cannabis infused sweetener or Cannabis infused elixir.

Water-Soluble Cannabinoid Composition

As a result of one invention method, a water-soluble cannabinoid composition is also provided that is bioavailable, fast acting and highly metabolizable made of a base oil, a Cannabis oil, at least one emulsifying agent and water.

The emulsifying agents in the cannabinoid composition are selected from the group consisting of xanthan gum, guar gum, cyclodextrin, lecithin, carrageen, monoglycerides, natural emulsifiers and organic emulsifiers that are safe for ingestion by humans.

The base oil in the cannabinoid composition is preferably selected from the group consisting of vegetable glycerine, coconut oil and any oil high in saturated fats. However, other nut oils such as almond oil, avocado oil, canola oil, coconut oil, corn oil, cottonseed oil, grapeseed oil, hazelnut oil, olive oil, extra virgin olive oil, palm oil, peanut oil, palm seed oil, pumpkin seed oil, safflower oil, sesame oil, soy oil, sunflower oil, vegetable oil and walnut oil can be used as the base oil.

A preferred emulsification used in the invention uses a base oil of coconut oil. Coconut oil is one of the best sources of healthy and "good" fatty acids.

The Cannabis oil in the composition is in a pure state that has been extracted from the marijuana plant by CO2 extraction, water extraction, butane extraction and extraction methods that leave a zero testing for residuals.

The Cannabis oil in the composition is selected from the group consisting of tetrahydrocannabinol (THC), cannabidiol (CBD) and other cannabinoid oils isolated from the marijuana plant.

Other ingredients such as chocolate and liquor can be added to the composition to provide different flavor profiles.

Method of Making the Emulsifications

A method to produce the invention emulsifications, includes first heating a base oil, preferably, extra virgin organic coconut oil to between about 120 to 220 degrees F. Pure extracted Cannabis oil is added to the heated oil but may be added to the oil prior to heating. In a high speed blender (or similar machine) an aqueous vehicle, preferably coconut water, is added to the coconut fat (oil) to ensure emulsification. While blending the heated mixture, adding at least one emulsifying agent in the amount of about 0.15% and about 2% of the total volume of finished product, to the heated oil to create a mixture. Percentages used herein are on a dry weight basis and are based on the total volume of the finished product. The blender is run at high speed for between about 30 seconds and about 2 minutes before adding the anhydrous caffeine in amounts ranging from about 10-300 mg. Alternatively, the caffeine can be added prior to adding the emulsifying agent or at the same time. The resulting cannabinoid emulsification is bio-available, highly metabolizable and fast acting when ingested by the user. The resulting emulsification is used to produce a line of THC and caffeine infused emulsifications. The invention process makes the Cannabis oil more bioavailable by making the oleo molecule water-soluble. Thus, upon ingestion, making it fast acting, taking effect in as little as about 15 minutes.

Other variations include various doses of Cannabis oil in the range of about 5 to 30 mg and different flavor profiles including lime, pomegranate, orange, lemon and others; and different serving sizes between about 1 and 64 oz.

The invention sweeteners are made by starting with high quality sweeteners including sugar, coconut sugar, date sugar, stevia, and any other quality sweeteners. The sweeteners are then infused with emulsified *Cannabis* oil using the process described below.

The *Cannabis* oil used is dissolved with alcohol, but it doesn't make the oil water-soluble. The invention emulsifying agents are needed to modify the *Cannabis* oil from its natural hydrophobic state to a "water-loving" hydrophilic state. The amount of *Cannabis* oil used depends on the desired potency, but preferably about 1 to about 10 grams of pure extracted *Cannabis* oil per pound of sweetener is used.

The amount of alcohol used in the invention process is typically 4 oz per lb of sugar. Preferably grain alcohol is used in the invention, although other similar alcohols can be used. At the end of the process there is zero alcohol residue in the resulting product.

The *Cannabis* oil is placed in a water bath and heated to between about 120 to 220 degrees F. for between about 4 and 30 minutes. The *Cannabis* oil is added to the alcohol and placed in a rotor blade machine and held at a temperature between about 120° F. and 220° F. for between about 1-7 minutes. During this process, an emulsifying agent, or combination of emulsifying agents, is then added to the heated mixture in an amount between about 0.15% to 3% of the total weight of the finished product.

This mixture is then combined with the sweetener and is heated to about 120 to about 220 degrees F. for about 10-60 minutes to complete the emulsification and to evaporate the residual alcohol from the sweetener. There is about 1 to about 4 grams of oil to about 4 oz of grain alcohol per pound of sweetener.

Possible variations include: percentage of emulsifier, from about 0.01% to 4%; the combination of emulsifiers to make up that percentage; the temperature and time as mentioned in previous section. These sweeteners provide a flexible, controllable, low-dose *Cannabis* experience, delivered in an understandable and desirable form. They can be used in beverages, such as coffee or tea.

The invention sweeteners assure that the THC is both fast acting and highly metabolizable. It assures that the consumer experiences a consistent experience from ingesting the product, instead of having a wide variation of experiences, including how long it takes to take effect, and how the effect will be each time.

The extracts of the invention can be mixed with other ingredients such as soda and other like liquids.

The process for making the *Cannabis* infused elixirs of the invention is as follows. The elixirs are essentially syrups, fruit syrups, and various flavored and unflavored syrups. The ingredients to make a batch of the invention elixirs include an emulsifying agent in the amount of about 0.12 to about 2%. A gallon of fruit syrup; flavored or unflavored and *Cannabis* oil in the amount between about 1000-2000 mg.

The syrup is heated to about 120-220 degrees F. The *Cannabis* oil is added to this heated mixture and blended in a rotor for about 1 to 7 minutes, during which time the emulsifier is added in. Each serving size has about 3 to 20 mg per ounce of water-soluble *Cannabis* oil.

Other variations include various doses of *Cannabis* oil in the range of about 5 to 30 mg and different flavor profiles including lime, pomegranate, orange, lemon and others; and different serving sizes between about 1 and about 64 oz.

The disclosure is further described with the help of the following examples. These examples, however, should not be construed to limit the scope of the disclosure.

Example 1

A *Cannabis* infused chocolate is provided that is bioavailable and delivers fast acting effects of the *Cannabis* when ingested. The method of making such includes use of about 5 to 10 oz of a base oil of either vegetable glycerine or coconut oil. A high quality liquor such as cognac or whiskey can be added but is optional. The base oil liquid is heated to between about 120 to 220° F. The *Cannabis* oil extract is added equal to about 110 to 1120 mg THC. The emulsifiers are added next, generally in the following amounts: about 0.5% lecithin, 0.15% xanthan gum, about 0.1% cyclodextrin. The emulsifiers can be used individually or in combination. The hot mixture is blended in a high speed blender or other machine, run on high speed for about 2 minutes. The mixture is allowed to cool to room temperature.

After the mixture has cooled, about 10 lb of melted chocolate is added and allowed to temper before depositing in a mold, then cooling to about 55° F.

Example 2

Several experiments were run using several different emulsifiers and combinations of different coconut oils: solid and liquid (MCT). (Note: liquid MCT is coconut oil that has medium chain triglyceride). Guar gum, lecithin, and cyclodextrin were tested as emulsifying agents and provided good results. However, xanthan gum was the most effective and provided the best emulsification of the oil and water, at the lowest viscosity.

The emulsification process that was determined the best had the added effect of making the THC more bioavailable by making the oleo molecule water-soluble. This had another added effect of making it fast acting, taking effect in as little as about 15 minutes.

The method used to produce the invention emulsifications, included first heating extra virgin organic coconut oil to between about 120 to about 220 degrees F. $CO_2$ extracted *Cannabis* oil is added. In a high speed blender (or similar machine) coconut water is added to the coconut fat (oil) to ensure emulsification. While blending, xanthan gum powder is added in an amount between about 0.15% and about 0.45% of the total volume of finished product. Percentages used herein are on a dry weight basis and are based on the total volume of the finished product. The blender is run at high speed for between 30 seconds and 2. The resulting emulsification is used to produce a variety of *Cannabis* infused products. The invention process makes the THC more bioavailable by making the oleo molecule water-soluble. Thus, upon ingestion, making it fast acting, taking effect in as little as 15 minutes.

Example 3

A variety of *Cannabis* infused products were prepared and tested in a random study group of 40 individuals. The products tested included *Cannabis* infused sugar, a cannabinoid/caffeine emulsification and a *Cannabis* infused elixir and are summarized in the tables below.

Each of the 40 individuals tested one of the products from Tables 2, 3 and 4. The breakdown of products tested was 10% (4 people) of the cannabinoid/caffeine emulsification;

20% (8 people) of cannabinoid elixirs and 70% (28 people) of the *Cannabis* infused sugar.

TABLE 2

Cannabis infused sugar (Serving size 1 tsp)

| | Sugar Product | | | | |
|---|---|---|---|---|---|
| | #1 | #2 | #3 | #4 | #5* |
| Cannabis Oil (mg/tsp) | 20 | 40 | 20 | 40 | 40 |
| Sugar (lbs) | 5 | 3 | 10 | 3 | 3 |
| Alcohol (oz) | 20 | 12 | 40 | 12 | 6 |
| Lecithin (%)** | 2 | 2 | 2 | 1 | 0 |
| Cyclodextrine (%)** | 0 | 0 | 0.03 | 0.12 | 0.25 |

*The sugar used in this sample was maple sugar.
**% of final product.

TABLE 3

Cannabinoid/caffeine emulsification (Serving size 2 oz)

| Component | Amount in emulsification |
|---|---|
| THC (per serving) | 10 mg |
| Coconut Fat (SOLID) | 2.75% |
| MCT | 0.65% |
| Coconut Water | 96% |
| Cyclodextrin | 0.12% |
| Xanthan Gum | 0.12% |
| Caffeine | 1000 mg |

*Lime and coconut extract were added for flavor

TABLE 4

Cannabinoid elixirs (flavored syrups) (Serving size 1 oz)

| Component | Amount in emulsification |
|---|---|
| THC | 10 mg/oz |
| Flavored syrup | 2.75% |
| Cyclodextrin | 0.16% |
| Xanthan Gum | 0.12% |
| Cannabis Oil | 0.04% |

Participants in the study were asked a series of questions, the results of which are summarized in the tables below. Q1. How long until you experienced an initial onset of effect after ingestion? The results are in Table 5. In all three products tested the onset of the *Cannabis* effects were less than 15-20 min.

TABLE 5

Results for Onset of Effect

| | Time | | | | | |
|---|---|---|---|---|---|---|
| | >10 min | 10-15 min | 15-20 min | 20-30 min | 30-40 min | <40 min |
| Sugar | 10.71% | 28.57% | 32% | 7.14% | 7.14% | 14.29% |
| Emulsification | 0 | 50% | 50% | 0 | 0 | 0 |
| Elixir | 12.4% | 25% | 25% | 25% | 12.5% | 0 |

Q2. On a scale of 1 to 5, the participants were asked to describe the strength of the initial onset experience after ingestion. A majority of respondents said the effects were mild to moderate. The results are in Table 6.

TABLE 6

Results for Strength

| | Time | | | | |
|---|---|---|---|---|---|
| | 1 No effect | 2 Very Mild | 3 Mild | 4 Moderate | 5 Strong |
| Sugar | 3.57% | 3.57% | 39.29%% | 46.43% | 7.14% |
| Emulsification | 0 | 0 | 50% | 50% | 0 |
| Elixir | 0 | 25% | 50% | 12.5% | 12.5% |

Q3. Compared to other *Cannabis* edibles, the participants were asked how they would characterize the rapidity of the onset of the products they tested. The respondents were comparing the invention products to other products they ingested including gummy bears, brownies and baked goods containing *Cannabis*. The results are in Table 7.

TABLE 7

Results for Comparison to Other Cannabis Edibles

| | Time | | | | |
|---|---|---|---|---|---|
| | 1 Much Slower | 2 Somewhat slower | 3 No difference | 4 Somewhat faster | 5 Much Faster |
| Sugar | 3.85% | 3.85% | 0 | 34.62% | 57.69% |
| Emulsification | 0 | 0 | 0 | 75% | 25% |
| Elixir | 0 | 0 | 0 | 25% | 75% |

In sum, in all embodiments, i.e. the *Cannabis* infused sugar, emulsification and elixir 92.7% to 100% said that the invention products acted faster than other *Cannabis* edibles.

The water-soluble cannabinoid composition and caffeine emulsifications of the invention provide a beneficial experience for people experiencing a variety of ailments: insomnia, muscle aches, anxiety, etc, or are in recovery from surgery, or in chemotherapy. The emulsifications make the *Cannabis* oil molecules hydrophilic, and thus water-soluble, which makes the THC bioavailable, faster acting, and more highly metabolizable.

Medical marijuana patients are often challenged by the mediums they are offered for consuming *Cannabis*. The water-soluble *Cannabis* of the invention provides them a convenient, and smokeless, alternative to access the cannabinoids they need to alleviate their ailments.

The foregoing description of various and preferred embodiments of the present invention has been provided for purposes of illustration only, and it is understood that numerous modifications, variations and alterations may be made without departing from the scope and spirit of the invention as set forth in the claims. The preceding examples can be repeated with similar success by substituting the generically or specifically described reactants and/or operating conditions of this invention for those used in the preceding examples.

Note that in the specification and claims, "about" or "approximately" means within twenty percent (20%) of the numerical amount cited.

Although the invention has been described in detail with particular reference to these embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An emulsion consisting essentially of isolated cannabidiol (CBD) or isolated tetrahydrocannabinol (THC); xanthan gum; cyclodextrin; glycerine; and coconut water.

2. The emulsion of claim 1, wherein the emulsion consists essentially of isolated cannabidiol; xanthan gum; cyclodextrin; glycerine; and coconut water.

3. The emulsion of claim 1, wherein the emulsion consists essentially of isolated tetrahydrocannabinol; xanthan gum; cyclodextrin; glycerine; and coconut water.

4. The emulsion of claim 1, wherein the emulsion consists essentially of 0.15% to 2% of the xanthan gum.

5. The emulsion of claim 1, wherein the emulsion consists essentially of 0.12% to 2% of the cyclodextrin.

6. The emulsion of claim 1, wherein the emulsion consists essentially of 20 mg of CBD and/or THC per ounce of emulsion.

7. The emulsion of claim 1, wherein the emulsion consists essentially of 30 mg of CBD and/or THC per ounce of emulsion.

8. The emulsion of claim 1, wherein the emulsion consists essentially of about 33% of CBD and/or THC.

9. The emulsion of claim 1, wherein the emulsion consists essentially of about 60% of coconut water.

* * * * *